United States Patent
Zeng et al.

(10) Patent No.: US 12,011,240 B2
(45) Date of Patent: Jun. 18, 2024

(54) SURGICAL ROBOTIC ARM CONTROL SYSTEM AND SURGICAL ROBOTIC ARM CONTROL METHOD

(71) Applicant: Metal Industries Research & Development Centre, Kaohsiung (TW)

(72) Inventors: Jian Jia Zeng, Kaohsiung (TW); Sheng-Hong Yang, Kaohsiung (TW); Bo-Wei Pan, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 450 days.

(21) Appl. No.: 17/518,541

(22) Filed: Nov. 3, 2021

(65) Prior Publication Data

US 2023/0081524 A1   Mar. 16, 2023

(30) Foreign Application Priority Data

Sep. 16, 2021 (TW) ................. 110134580

(51) Int. Cl.
*A61B 34/32* (2016.01)
*A61B 34/20* (2016.01)
(Continued)

(52) U.S. Cl.
CPC ............. *A61B 34/32* (2016.02); *G06T 7/20* (2013.01); *G06T 7/50* (2017.01); *G06T 7/73* (2017.01);
(Continued)

(58) Field of Classification Search
CPC . A61B 34/32; A61B 90/50; A61B 2034/2057; A61B 2034/2065;
(Continued)

(56) References Cited

U.S. PATENT DOCUMENTS 6,304,050 B1 * 10/2001 Skaar .................... B25J 9/1692
901/3
6,683,677 B2 * 1/2004 Chon ....................... G06T 7/80
356/28
(Continued)

FOREIGN PATENT DOCUMENTS

CN   102802551   11/2012
CN   104661612   5/2015
(Continued)

OTHER PUBLICATIONS

"Office Action of Taiwan Counterpart Application", issued on Mar. 16, 2022, p. 1-p. 5.

*Primary Examiner* — Bhavesh V Amin
(74) *Attorney, Agent, or Firm* — JCIPRNET

(57) ABSTRACT

A surgical robotic arm control system and a surgical robotic arm control method are provided. The surgical robotic arm control system includes a surgical robotic arm, a first image capturing unit, a second image capturing unit, and a processor. The first image capturing unit is used for obtaining a field image. The field image includes a first target image of a target object. The second image capturing unit is disposed at an end position of the surgical robotic arm and is used to obtain a second target image of the target object. The processor analyzes the field image to obtain robotic arm movement information, and controls the surgical robotic arm to move to approach the target object. The processor analyzes the target image to obtain robotic arm rotation information, and controls an angle and a posture of the surgical robotic arm.

20 Claims, 6 Drawing Sheets

(51) Int. Cl.
   *A61B 90/50* (2016.01)
   *G06T 7/20* (2017.01)
   *G06T 7/50* (2017.01)
   *G06T 7/73* (2017.01)
   *G06V 20/10* (2022.01)
   *G06V 40/10* (2022.01)
   *H04N 23/90* (2023.01)

(52) U.S. Cl.
   CPC ............ *G06V 20/10* (2022.01); *G06V 40/107* (2022.01); *H04N 23/90* (2023.01); *A61B 2034/2057* (2016.02); *A61B 2034/2065* (2016.02); *A61B 90/50* (2016.02); *G06T 2207/10028* (2013.01); *G06T 2207/30196* (2013.01); *G06V 2201/034* (2022.01)

(58) Field of Classification Search
   CPC .............. A61B 2090/364; A61B 34/20; A61B 2034/2055; A61B 2090/067; A61B 34/30; G06T 7/20; G06T 7/50; G06T 7/73; G06T 2207/10028; G06T 2207/30196; G06T 7/74; G06T 7/248; G06T 2207/10016; G06T 2207/20081; G06T 2207/20084; G06T 2207/30204; G06V 20/10; G06V 40/107; G06V 2201/034; H04N 23/90
   See application file for complete search history.

(56) References Cited

U.S. PATENT DOCUMENTS

| | | | | |
|---|---|---|---|---|
| 8,386,089 | B2* | 2/2013 | Ogren | G05D 1/0038 |
| | | | | 701/2 |
| 9,019,376 | B2* | 4/2015 | Lee | H04N 7/185 |
| | | | | 348/148 |
| 9,386,209 | B2* | 7/2016 | Kim | G06T 7/73 |
| 9,595,207 | B2* | 3/2017 | Kesavadas | G09B 23/28 |
| 10,074,031 | B2* | 9/2018 | Krenzer | G06T 3/40 |
| 10,901,431 | B1* | 1/2021 | Ebrahimi Afrouzi | |
| | | | | G05D 1/0246 |
| 11,072,074 | B2* | 7/2021 | Shivaram | B25J 9/1697 |
| 11,291,508 | B2* | 4/2022 | O'Hara | A61B 5/0071 |
| 11,435,305 | B2* | 9/2022 | Wang | G06T 7/0004 |
| 2003/0144765 | A1* | 7/2003 | Habibi | G06T 1/0007 |
| | | | | 700/259 |
| 2005/0065653 | A1* | 3/2005 | Ban | B25J 9/1697 |
| | | | | 700/245 |
| 2006/0178559 | A1* | 8/2006 | Kumar | G16H 40/63 |
| | | | | 600/109 |
| 2007/0167702 | A1* | 7/2007 | Hasser | A61B 90/36 |
| | | | | 600/407 |
| 2009/0036902 | A1* | 2/2009 | DiMaio | A61B 8/12 |
| | | | | 606/130 |
| 2009/0177452 | A1* | 7/2009 | Ullrich | G06F 3/014 |
| | | | | 703/11 |
| 2009/0202174 | A1* | 8/2009 | Shiba | G06V 10/48 |
| | | | | 382/282 |
| 2010/0121483 | A1* | 5/2010 | Junghans | B65G 61/00 |
| | | | | 700/218 |
| 2010/0167248 | A1* | 7/2010 | Ryan | H04N 7/181 |
| | | | | 434/262 |
| 2010/0172733 | A1* | 7/2010 | Chalubert | A61F 4/00 |
| | | | | 414/730 |
| 2011/0280472 | A1* | 11/2011 | Wallack | G06T 7/80 |
| | | | | 901/14 |
| 2013/0274921 | A1* | 10/2013 | Aiso | B25J 9/1697 |
| | | | | 700/251 |
| 2013/0295540 | A1* | 11/2013 | Kesavadas | G09B 23/28 |
| | | | | 434/262 |
| 2015/0213617 | A1* | 7/2015 | Kim | H04N 23/57 |
| | | | | 382/103 |
| 2015/0265143 | A1* | 9/2015 | Yoon | A61B 1/0014 |
| | | | | 600/104 |
| 2016/0291571 | A1* | 10/2016 | Cristiano | B25J 9/1697 |
| 2017/0017839 | A1* | 1/2017 | Hiramatsu | B25J 9/1697 |
| 2017/0176999 | A1* | 6/2017 | Bobda | G05D 1/0297 |
| 2018/0139431 | A1* | 5/2018 | Simek | H04N 13/271 |
| 2018/0161984 | A1* | 6/2018 | Ishige | B25J 9/1697 |
| 2018/0165833 | A1* | 6/2018 | Inoue | H04N 17/002 |
| 2018/0342100 | A1* | 11/2018 | Mollis | G06T 3/4038 |
| 2019/0015988 | A1* | 1/2019 | Inazumi | B25J 9/1697 |
| 2019/0020817 | A1* | 1/2019 | Shan | H04N 23/698 |
| 2019/0099222 | A1 | 4/2019 | Nahum et al. | |
| 2019/0176335 | A1* | 6/2019 | Shivaram | B25J 9/1692 |
| 2019/0199915 | A1* | 6/2019 | Coiseur | A61B 34/20 |
| 2019/0291277 | A1* | 9/2019 | Oleynik | B25J 9/1669 |
| 2019/0350661 | A1 | 11/2019 | Fukushima et al. | |
| 2019/0384303 | A1* | 12/2019 | Muller | G06N 20/00 |
| 2019/0388160 | A1* | 12/2019 | Wood | G01J 3/0229 |
| 2020/0094405 | A1 | 3/2020 | Davidson et al. | |
| 2020/0178774 | A1* | 6/2020 | Komp | G06T 19/003 |
| 2020/0222146 | A1* | 7/2020 | Komp | A61B 1/000094 |
| 2021/0007825 | A1* | 1/2021 | Sela | G06T 7/80 |
| 2021/0016444 | A1* | 1/2021 | Martin | B25J 9/1653 |
| 2021/0026368 | A1* | 1/2021 | Cochran | G06T 7/593 |
| 2021/0089040 | A1* | 3/2021 | Ebrahimi Afrouzi | |
| | | | | A47L 9/2873 |
| 2021/0298590 | A1* | 9/2021 | Ayvali | A61B 34/30 |
| 2021/0406551 | A1* | 12/2021 | Barral | H04N 21/4316 |
| 2022/0079687 | A1* | 3/2022 | Sexson | A61B 34/20 |
| 2023/0097932 | A1* | 3/2023 | Chen | B25J 9/1674 |
| | | | | 700/254 |
| 2024/0062395 | A1* | 2/2024 | Robinson | H04N 7/181 |
| 2024/0066712 | A1* | 2/2024 | Gao | G06T 7/593 |

FOREIGN PATENT DOCUMENTS

| | | |
|---|---|---|
| CN | 107708598 | 2/2018 |
| CN | 107981872 | 5/2018 |

* cited by examiner

SURGICAL ROBOTIC ARM CONTROL SYSTEM AND SURGICAL ROBOTIC ARM CONTROL METHOD

CROSS-REFERENCE TO RELATED APPLICATION

This application claims the priority benefit of Taiwan application serial no. 110134580, filed on Sep. 16, 2021. The entirety of the above-mentioned patent application is hereby incorporated by reference herein and made a part of this specification.

BACKGROUND

Technical Field

The disclosure relates to a mechanical control technology, and in particular to a surgical robotic arm control system and a surgical robotic arm control method.

Description of Related Art

With the advancements in the development of medical apparatuses, related medical apparatuses that may be automatically controlled, which may facilitate efficiency in performing surgeries for medical workers, are currently one of the important development directions in this field. In particular, a surgical robotic arm used to assist or cooperate with a medical worker (operator) to perform related surgical work in the surgical process is even more important. However, in the existing surgical robotic arm design, in order to achieve automatic control functions on the surgical robotic arm, the surgical robotic arm has to be disposed with multiple sensors, and the user has to perform a complicated manual calibration operation in each surgical process, so that the surgical robotic arm may avoid obstacles in the path during the movement process to realize accurate automatic movement and automatic operation results.

SUMMARY

In view of the above, the disclosure provides a surgical robotic arm control system and a surgical robotic arm control method, which effectively control a surgical robotic arm to move at a corresponding angle and posture and approach a target object.

A surgical robotic arm control system of the disclosure includes a surgical robotic arm, a first image capturing unit, a second image capturing unit, and a processor. The surgical robotic arm has a plurality of joint shafts. The first image capturing unit is used to obtain a field image. The field image comprises a first target image of a target object. The second image capturing unit is disposed at an end position of the surgical robotic arm and is used to obtain a second target image of the target object. The processor is coupled to the surgical robotic arm, the first image capturing unit, and the second image capturing unit, and is used to execute a plurality of modules. The processor analyzes the field image to obtain robotic arm movement information, and controls the surgical robotic arm to move to approach the target object according to the robotic arm movement information. The processor analyzes the second target image to obtain robotic arm rotation information, and controls an angle and a posture of the surgical robotic arm according to the robotic arm rotation information to match with the target object.

A surgical robotic arm control method of the disclosure includes the following. A field image is obtained through a first image capturing unit, and the field image comprises a first target image of a target object. A second target image of the target object is obtained through a second image capturing unit, and the second image capturing unit is disposed at an end position of a surgical robotic arm. The field image is analyzed through a processor to obtain robotic arm movement information. The surgical robotic arm is controlled through the processor to move to approach the target object according to the robotic arm movement information. The target image is analyzed through the processor to obtain robotic arm rotation information. An angle and a posture of the surgical robotic arm are controlled to match with the target object through the processor according to the robotic arm rotation information.

Based on the above, in the surgical robotic arm control system and the surgical robotic arm control method of the disclosure, the surgical robotic arm is automatically controlled through computer vision image technology to move and approach the target object, and the angle and posture of the surgical robotic arm are controlled so that the surgical robotic arm is matched with the target object.

To provide a further understanding of the above features and advantages of the disclosure, embodiments accompanied with drawings are described below in details.

DESCRIPTION OF THE EMBODIMENTS

Figure 1:
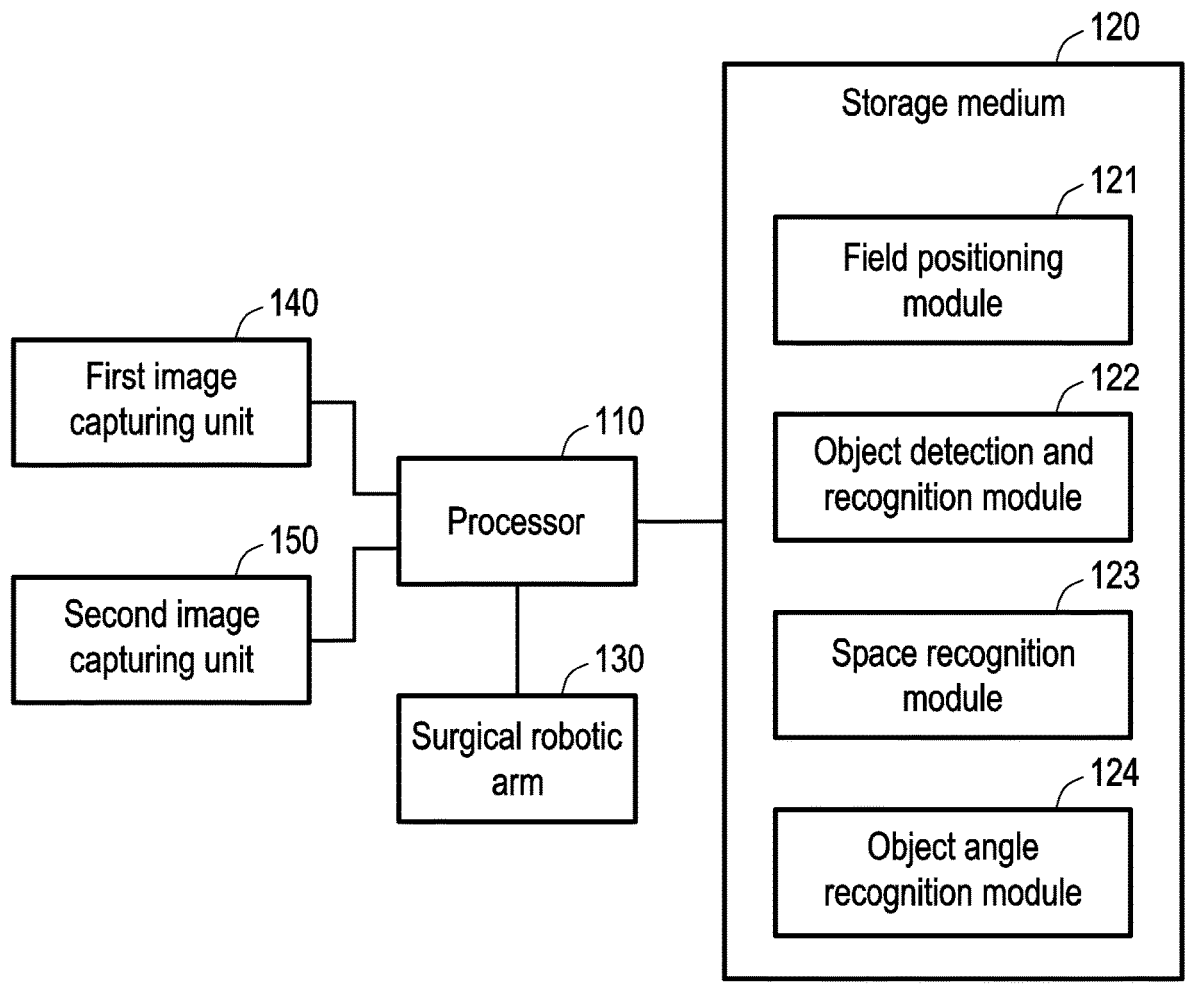
FIG. 1 is a schematic circuit diagram of a surgical robotic arm control system according to an embodiment of the disclosure.

To provide a further understanding of the content of the disclosure, embodiments as examples of how this disclosure may be implemented are described below. In addition, wherever possible, elements/components/steps with the same reference numeral in the drawings and embodiments represent the same or similar components.

FIG. 1 is a schematic circuit diagram of a surgical robotic arm control system according to an embodiment of the disclosure. Referring to FIG. 1, a surgical robotic arm control system 100 includes a processor 110, a storage medium 120, a surgical robotic arm 130, a first image capturing unit 140, and a second image capturing unit 150. The processor 110 is coupled to the storage medium 120, the surgical robotic arm 130, the first image capturing unit 140, and the second image capturing unit 150. The storage medium 120 may store a field positioning module 121, an object detection and recognition module 122, a space recognition module 123, and an object angle recognition module 124. In this embodiment, the surgical robotic arm control system 100 is adapted for being operated in a surgical setting. The first image capturing unit 140 and the second image capturing unit 150 may respectively obtain a real-time operation image and provide the same to the processor 110 so that the processor 110 may analyze the real-time operation image and identify a target object through image recognition by computer vision.

In this embodiment, the processor 110 may automatically control the movement of the surgical robotic arm 130 correspondingly according to the identification result of the target object, and allow the surgical robotic arm 130 to approach the target object. In this embodiment, the target object may be, for example, a hand object or an instrument object. The hand object refers to a palm of a medical worker. The instrument object refers to a medical surgical instrument. In this regard, the surgical robotic arm 130 of the embodiment is adapted for being combined with or connected to the medical surgical instrument to facilitate the operation of the surgery. For example, an end of the surgical robotic arm 130 has a hook, and the hook of the surgical robotic arm 130 may hook a medical surgical instrument to allow the medical surgical instrument to be fixed to a surgical subject in a specific state, or to achieve a certain surgical function. Therefore, the surgical robotic arm control system 100 of this embodiment may operate the surgical robotic arm 130 to automatically approach the palm of the medical worker or the medical surgical instrument, so that the medical worker may grasp or use the end of the surgical robotic arm 130 to combine or connect the same with the medical surgical instrument. In addition, the surgical robotic arm 130 may automatically avoid obstacles in the moving process. Therefore, the surgical robotic arm control system 100 of this embodiment may realize automatic surgical assistance functions.

In this embodiment, the processor 110 may be, for example, a central processing unit (CPU), or other programmable general-purpose or special-purpose devices including a micro-processor, a digital signal processor (DSP), an image processor unit (IPU), a graphics processing unit (GPU), a programmable controller, application specific integrated circuits (ASIC), a programmable logic device (PLD), other similar processing devices or a combination of these devices.

In this embodiment, the storage medium 120 may be a memory, such as a dynamic random access memory (DRAM), a flash memory, or a non-volatile random access memory (NVRAM), and the disclosure is not limited thereto. The storage medium 120 may store a related algorithm of the field positioning module 121, the object detection and recognition module 122, the space recognition module 123, and the object angle recognition module 124, and may further store related algorithms, programs, and data that are used to implement the control function of the surgical robotic arm of the disclosure, including image data, a robotic arm control command, a robotic arm control software, and a computing software. In this embodiment, the field positioning module 121, the object detection and recognition module 122, the space recognition module 123, and the object angle recognition module 124 may be neural network modules that respectively implement corresponding functions.

In this embodiment, the field positioning module 121 may, for example, execute a camera calibration operation to realize a coordinate system matching function between the surgical robotic arm 130 and the first image capturing unit 140. The object detection and recognition module 122 may be realized, for example, by executing a fully convolutional network (FCN) algorithm. The space recognition module 123 may be realized, for example, by executing an algorithm of depth reinforcement learning (Deep Q Network, DQN), deterministic policy gradient (DDPG), or asynchronous advantage actor-critic (A3C).

In this embodiment, the surgical robotic arm 130 has a plurality of joint shafts. The surgical robotic arm 130 may be a robotic arm with six degrees of freedom tracking (6 DOF), and the processor 110 may execute a machine learning module which applies the Markov decision process to control the surgical robotic arm 130. In this embodiment, the first image capturing unit 140 may be, for example, a depth camera, and may be used to capture a surgical field to obtain the field image and its depth information. In this embodiment, the second image capturing unit 150 may be a camera, and may be disposed at an end of the surgical robotic arm 130 to capture the target object at close range to obtain the target image.

Figure 2:
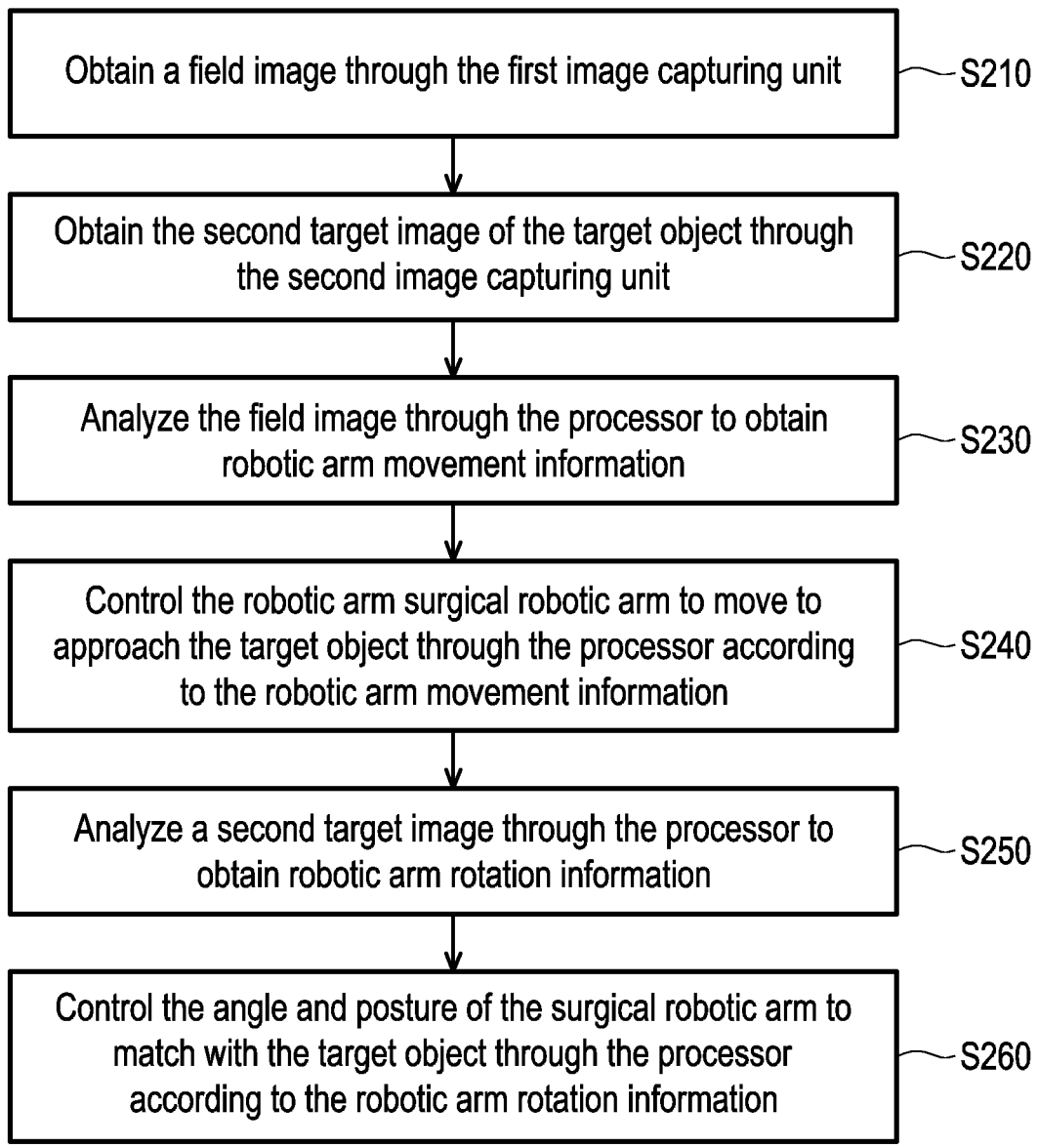
FIG. 2 is a flow chart of a surgical robotic arm control method according to an embodiment of the disclosure.
Figure 3:
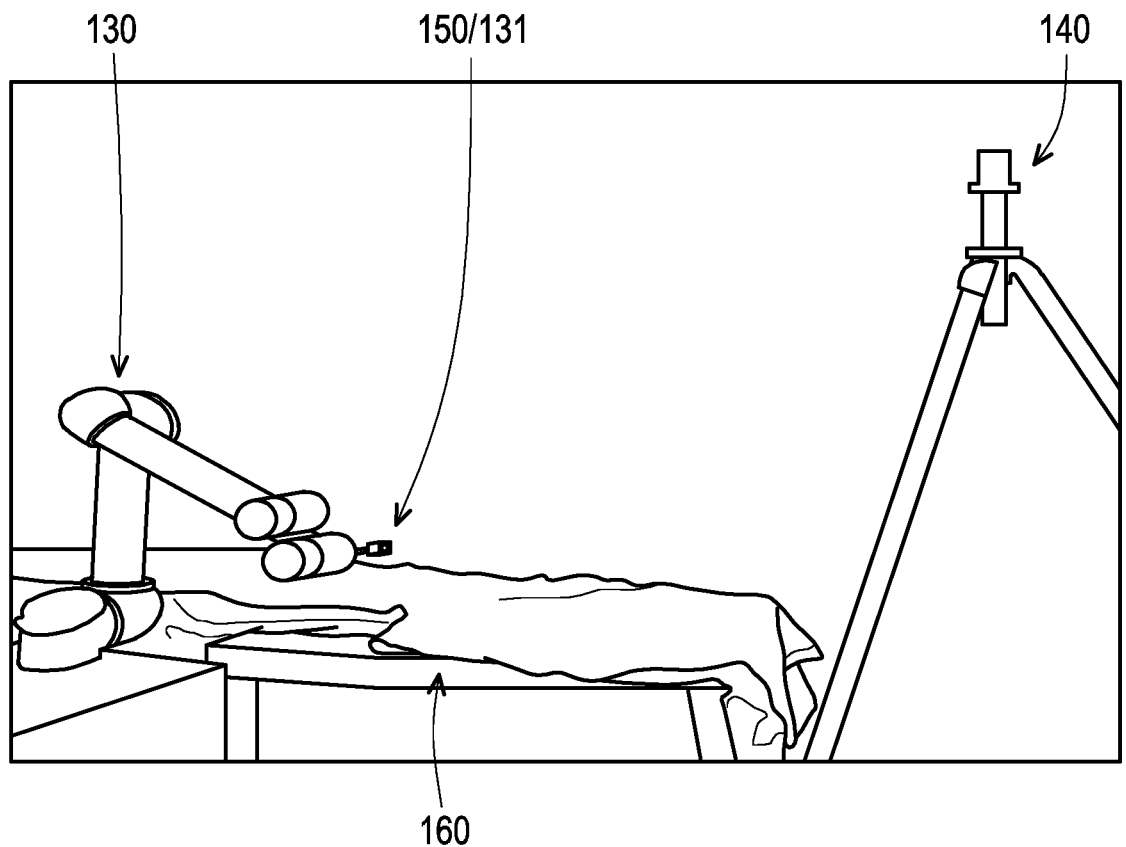
FIG. 3 is a schematic view of a configuration of a surgical robotic arm control system according to an embodiment of the disclosure.

FIG. 2 is a flow chart of a surgical robotic arm control method according to an embodiment of the disclosure. Referring to FIGS. 1 and 2, the surgical robotic arm control system 100 may execute steps S210 to S260 to realize a control function of the surgical robotic arm. First, referring to FIG. 3, which is a schematic view of a configuration of a surgical robotic arm control system according to an embodiment of the disclosure. The surgical robotic arm control system 100 may be applied in the surgical field as shown in FIG. 3. In this embodiment, the surgical robotic arm control system 100 may be disposed around an operating table 160. There is a fixed position relationship between the surgical robotic arm 130, the first image capturing unit 140, and the operating table 160. The second image capturing unit 150 may be disposed at an end 131 of the surgical robotic arm 130.

In this embodiment, the first image capturing unit 140 may obtain a plurality of positioning images and reference depth information in advance, and the plurality of positioning images may include a positioning object. In this regard, the user may, for example, use a positioning board with a pattern of a checkerboard image as the positioning object, and place the same on the operating table 160, so that the plurality of positioning images may respectively include the pattern of a checkerboard image. The number of positioning images may be 5, for example. Next, the processor 110 may execute the field positioning module 121 to analyze the positioning coordinate information (a plurality of spatial coordinates) and the reference depth information of the respective positioning objects in the plurality of positioning images through the field positioning module 121 to match the camera coordinate system (spatial coordinate system) of the first image capturing unit 140 with the robotic arm coordinate system (spatial coordinate system) of the surgical robotic arm 130. The processor 110 may match the camera coordinate system of the first image capturing unit 140 with the robotic arm coordinate system of the surgical robotic arm 130 according to the fixed position relationship, positioning coordinate information, and reference depth information.

Figure 4:
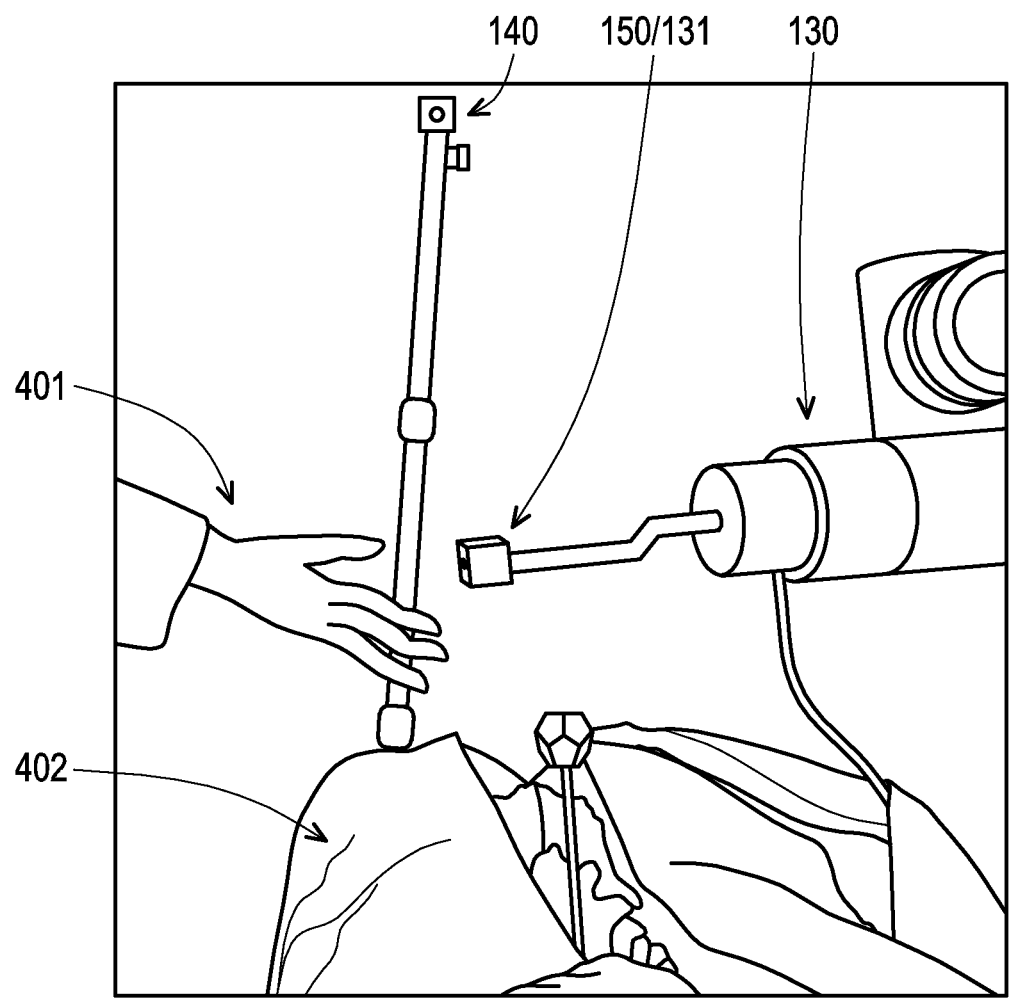
FIG. 4 is a schematic view of a control surgical robotic arm approaching a target object according to an embodiment of the disclosure.
Figure 5:
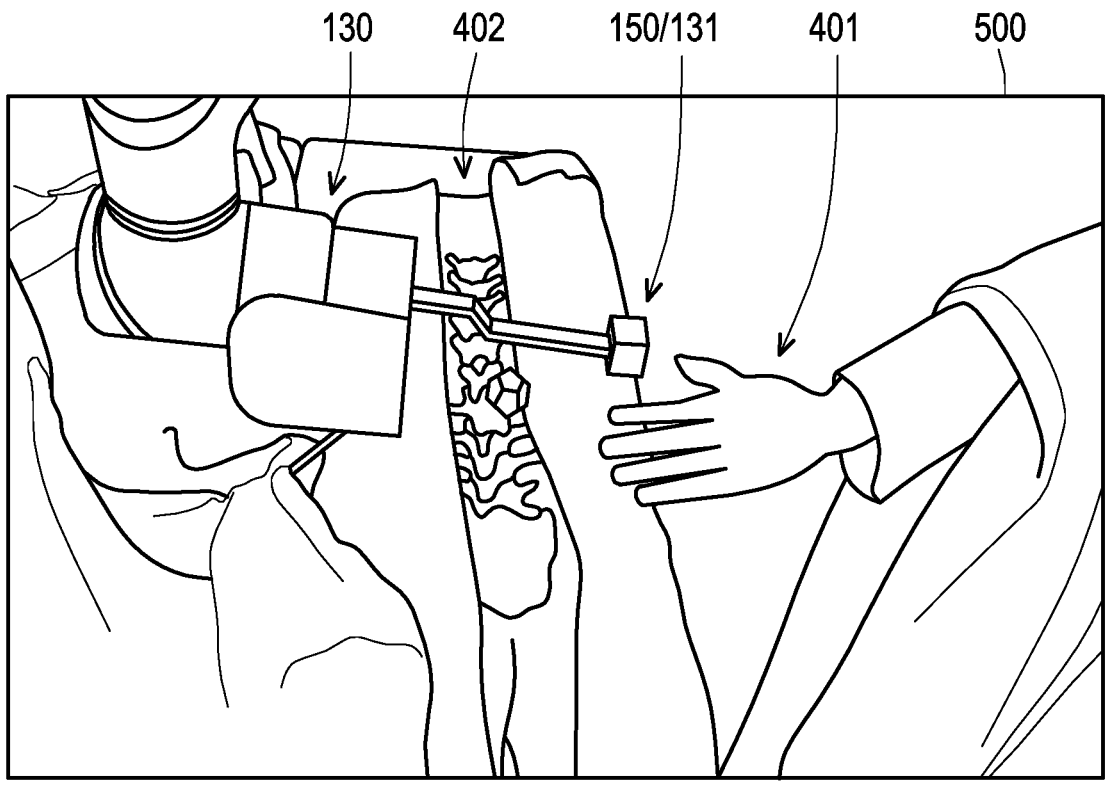
FIG. 5 is a schematic view of a field image according to an embodiment of the disclosure.
Figure 6:
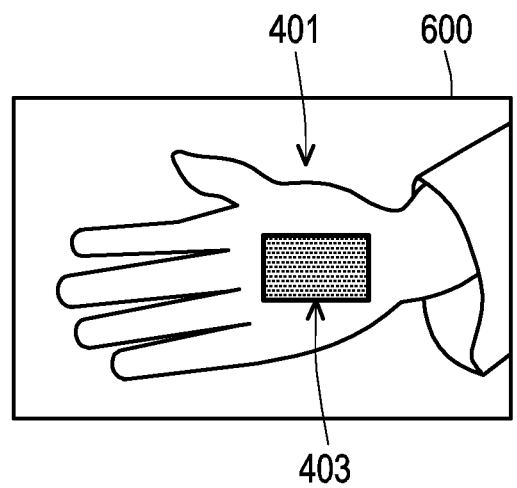
FIG. 6 is a schematic view of a second target image according to an embodiment of the disclosure.

Next, after the coordinate systems of the first image capturing unit 140 and the surgical robotic arm 130 are matched, the surgical robotic arm control system 100 may be implemented in a surgical setting. Referring to FIG. 4, FIG. 4 is a schematic view of a control surgical robotic arm approaching a target object according to an embodiment of the disclosure. In this embodiment, a surgery subject 402 may be placed on the operating table, and a hand object 401 may perform surgery on the surgery subject 402. The hand object 401 is the hand of a medical worker. Referring to FIG. 5, FIG. 5 is a schematic view of a field image according to an embodiment of the disclosure. In step S210, the surgical robotic arm control system 100 may obtain a field image 500 as shown in FIG. 5 through the first image capturing unit 140. The field image 500 includes a first target image (corresponding to a sub-image of the hand object 401) of the target object (the hand object 401), and may further include the image of the surgical robotic arm 130, the second image capturing unit 150, and the surgery subject 402. In this embodiment, the surgical robotic arm control system 100 may further include an input unit. The input unit is coupled to the processor 110 to provide a selection signal, so that the processor 110 may select an image range of the first target image corresponding to the target object from the field image 500 according to the selected signal. Next, referring to FIG. 6, FIG. 6 is a schematic view of a second target image according to an embodiment of the disclosure. In step S220, the surgical robotic arm control system 100 may obtain the second target image 500 of the target object (the hand object 401) as shown in FIG. 6 through the second image capturing unit 150.

In step S230, the surgical robotic arm control system 100 may analyze the field image 500 through the processor 110 to obtain robotic arm movement information. In this embodiment, the processor 110 may execute the object detection and recognition module 122 to analyze the first target image (corresponding to the sub-image of the hand object 401) and the corresponding target depth information in the field image 500 through the object detection and recognition module 122 to obtain the coordinate information (spatial coordinates) of the target object (the hand object 401). The processor 110 further identifies obstacles in the field image 500. The processor 110 may execute the space recognition module 123 to analyze the first target image (corresponding to the sub-image of the hand object 401), target depth information, at least one obstacle image, and at least one piece of obstacle depth information in the field image 500 through the space recognition module 123 to obtain effective spatial feature weight information. Therefore, the processor 110 may generate robotic arm movement information according to the coordinate information and the effective spatial feature weight information. In other words, the processor 110 of this embodiment may identify the effective spatial feature value and obstacle range in the surgical environment through digital image superimposition by computer vision and a machine learning algorithm, and may predict directions to avoid obstacles and select an optimal path from the directions, so that the surgical robotic arm 130 may automatically move away from environment-related objects and reach the specified target position (approaching the target object).

In step S240, the surgical robotic arm control system 100 may control the robotic arm surgical robotic arm 130 to move and approach the target object (the hand object 401) through the processor 110 according to the robotic arm movement information. In this embodiment, the processor 110 may project a surgical space range through computer vision, and deduce a position to which the surgical robotic arm 130 may move in the space range. In addition, the processor 110 may achieve the intelligent decision-making effect of the surgical robotic arm 130 by using neural network operations. For example, the processor 110 may execute an object image processing/recognition module, a neural network related algorithm, or a surgical space image processing module, or deduce the effective moving space range, the three-dimensional position, or the transformation matrix of the surgical robotic arm 130 through neural network. Therefore, the processor 110 may effectively control the surgical robotic arm 130 to move and automatically avoid obstacles so as to stably approach the target object (the hand object 401).

In step S250, the surgical robotic arm control system 100 may analyze a second target image 600 through the processor 110 to obtain robotic arm rotation information. In this embodiment, the processor 110 may execute the object angle recognition module 124 to analyze the second target image 600 through the object angle recognition module 124 to obtain the angle information of the target object (the hand object 401), and the processor 110 may generate the robotic arm rotation information according to the angle information. The processor 110 may create an object recognition model to identify the angle and posture that match with the surgical robotic arm 130 according to the shape, edge, and area of the target object based on the second target image 600 obtained by the second image capturing unit 150 (end angle of view capturing unit). Specifically, as shown in FIG. 6, the palm position of the hand object 401 may include a feature block, and the feature block may be, for example, a pattern (for example, a rectangle) with a specific shape drawn on a surgical glove. The object angle recognition module 124 may analyze the shape of a feature block image 403 in the second target image 600 to deduce the posture of the hand object 401 through the deformation analysis results (for example, changes in the four side lengths and changes in the four angles, etc.) of the shape of the feature block image 403, and obtain the angle information (for example, the angle of the palm facing up or down) corresponding to the hand object 401.

In addition, the object detection and recognition module 122 may output a plurality of first feature weights based on the field image 500, and the object angle recognition module 124 may output a plurality of second feature weights based on the second target image 600. In this embodiment, the processor 110 may compare these first feature weights and these second feature weights to determine standard recognition information corresponding to the target object. Specifically, the plurality of first feature weights and the plurality of second feature weights may, for example, respectively include the feature weight of color, shape, and edge. The processor 110 may establish a feature weight table based on these feature weights to determine, for example, indexes greater than 0.9, and sort these feature weights respectively. After the processor 110 adds up a number of (for example, 3) largest feature weights, a plurality of feature weights with the largest values are used as determination criterion recognition information. Therefore, the surgical robotic arm control system 100 of this embodiment may link and share the features of the object detection and recognition module 122 and the object angle recognition module 124 to simultaneously recognize the same target object, which may effectively reduce misjudgments.

In step S260, the surgical robotic arm control system 100 may control the angle and posture of the surgical robotic arm 130 to match with the target object through the processor 110 according to the robotic arm rotation information. In this embodiment, as shown in FIG. 5, the processor 110 may, for example, train the origin position of the end 131 of the surgical robotic arm 130 to automatically move to the vicinity of the target object (the hand object 401) or the target position of the surgical operation point by using a depth reinforcement learning (Deep Q Network, DQN) module. Therefore, the surgical robotic arm control system 100 and the surgical robotic arm control method of this embodiment may realize the following: in the process of a medical worker performing surgery on the surgery subject 402, the surgical robotic arm 130 may automatically move to the vicinity of the target object (for example, the palm of the medical worker), so that the medical worker may conveniently and quickly operate an auxiliary medical object disposed at the end of the surgical robotic arm 130. The auxiliary medical object may be, for example, related surgical equipment in the surgical process, and the disclosure is not limited thereto. The surgical robotic arm control system 100 and the surgical robotic arm control method of this embodiment may realize automated and highly efficient medical surgery assistance functions.

Figure 7:
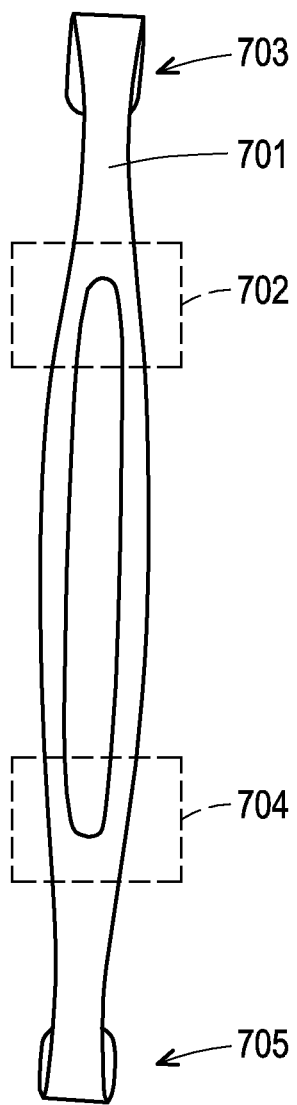
FIG. 7 is a schematic view of a target object and a groove section according to another embodiment of the disclosure.

FIG. 7 is a schematic view of a target object and a groove section according to another embodiment of the disclosure. In another embodiment of the disclosure, the aforementioned target object may be an instrument object 701 as shown in FIG. 7, and the instrument object 701 includes a groove section 702 and a groove section 704. The above-mentioned second target image may display the instrument object 701 as shown in FIG. 7. In addition, the object angle recognition module 124 in FIG. 1 may analyze an image including the groove section 702 and/or the groove section 704 in the second target image to obtain the angle information of the target object. The processor 110 may, for example, analyze the size, direction, and angle of the groove section 702 and/or the groove section 704 to estimate the posture of the instrument object 701. It should be noted that the instrument object 701 may further include a groove portion 703 and a groove portion 705. One of the groove portion 703 and the groove portion 705 may be used to hook the surgical site. In other words, in the process of a medical worker performing surgery on the surgical subject, the surgical robotic arm may automatically move to the vicinity of the instrument object 701 to allow the medical worker to conveniently and quickly hook the surgical robotic arm to the groove section 702 or the groove section 704 of the instrument object 701, and may hook the groove portion 703 or the groove portion 705 to one side of the surgical site (the other side of the surgical site may also be hooked, for example, by another instrument object) to spread open the wound, thereby providing auxiliary surgical functions (for example, spreading the surgical site open).

In summary, the surgical robotic arm control system and the surgical robotic arm control method of the disclosure may automatically control the surgical robotic arm to move and approach the target object through two image capturing units by using computer vision image technology, and may also control the angle and posture of the surgical robotic arm according to the current posture of the target object to match the surgical robotic arm with the target object, so that the medical worker may conveniently, quickly and easily use the surgical robotic arm to assist the operation process during surgery.

Although the disclosure has been disclosed in the above by way of embodiments, the embodiments are not intended to limit the disclosure. Those with ordinary knowledge in the technical field can make various changes and modifications without departing from the spirit and scope of the disclosure. Therefore, the protection scope of the disclosure is subject to the scope of the appended claims.

What is claimed is:

1. A surgical robotic arm control system, comprising:
   a surgical robotic arm, having a plurality of joint shafts;
   a first image capturing unit, used to obtain a field image, wherein the field image comprises a first target image of a target object;
   a second image capturing unit, disposed at an end position of the surgical robotic arm, used to obtain a second target image of the target object; and
   a processor, coupled to the surgical robotic arm, the first image capturing unit, and the second image capturing unit, used to execute a plurality of modules,
   wherein the processor analyzes the field image to obtain robotic arm movement information, and controls the surgical robotic arm to move to approach the target object according to the robotic arm movement information,
   wherein the processor analyzes the second target image to obtain robotic arm rotation information, and controls an angle and a posture of the surgical robotic arm according to the robotic arm rotation information to match with the target object.

2. The surgical robotic arm control system according to claim 1, wherein the first image capturing unit is a depth camera, the first image capturing unit obtains a positioning image and reference depth information in advance, and the positioning image comprises a positioning object,
   wherein the processor executes a field positioning module to analyze positioning coordinate information and the reference depth information of the positioning object in the positioning image through the field positioning module, so that a camera coordinate system of the depth camera and a robotic arm coordinate system of the surgical robotic arm are matched.

3. The surgical robotic arm control system according to claim 2, wherein the surgical robotic arm control system is disposed around an operating table, and there is a fixed position relationship between the surgical robotic arm, the first image capturing unit, and the operating table, so that the processor matches the camera coordinate system of the depth camera with the robotic arm coordinate system of the surgical robotic arm according to the fixed position relationship, the positioning coordinate information, and the reference depth information.

4. The surgical robotic arm control system according to claim 2, wherein the processor executes an object detection and recognition module to analyze the first target image in the field image and corresponding target depth information through the object detection and recognition module to obtain coordinate information of the target object.

5. The surgical robotic arm control system according to claim 4, wherein the processor executes a space recognition module to analyze the first target image, the target depth information, at least one obstacle image, and at least one piece of obstacle depth information in the field image through the space recognition module to obtain effective spatial feature weight information, and the processor generates the robotic arm movement information according to the coordinate information and the effective spatial feature weight information.

6. The surgical robotic arm control system according to claim 4, wherein the processor executes an object angle recognition module to analyze the second target image through the object angle recognition module to obtain angle information of the target object, and the processor generates the robotic arm rotation information according to the angle information.

7. The surgical robotic arm control system according to claim 6, wherein the target object is a hand object, and the hand object comprises a feature block, wherein the object angle recognition module analyzes a feature block image in the second target image to obtain the angle information of the target object.

8. The surgical robotic arm control system according to claim 6, wherein the target object is an instrument object, and the instrument object comprises a groove section, wherein the object angle recognition module analyzes a groove section image in the second target image to obtain the angle information of the target object.

9. The surgical robotic arm control system according to claim 6, wherein the object detection and recognition module outputs a plurality of first feature weights according to the field image, and the object angle recognition module outputs a plurality of second feature weights according to the second target image,
wherein the processor compares the first feature weights and the second feature weights to determine standard recognition information corresponding to the target object.

10. The surgical robotic arm control system according to claim 1, further comprising:
an input unit, coupled to the processor to provide a selection signal, so that the processor selects an image range of the first target image corresponding to the target object from the field image according to the selection signal.

11. A surgical robotic arm control method, comprising:
obtaining a field image through a first image capturing unit, wherein the field image comprises a first target image of a target object;
obtaining a second target image of the target object through a second image capturing unit, wherein the second image capturing unit is disposed at an end position of a surgical robotic arm;
analyzing the field image through a processor to obtain robotic arm movement information;
controlling the surgical robotic arm to move to approach the target object through the processor according to the robotic arm movement information;
analyzing the target image through the processor to obtain robotic arm rotation information; and
controlling an angle and a posture of the surgical robotic arm to match with the target object through the processor according to the robotic arm rotation information.

12. The surgical robotic arm control method according to claim 11, wherein the first image capturing unit is a depth camera, wherein the surgical robotic arm control method further comprises:
obtaining a positioning image and reference depth information in advance through the first image capturing unit, wherein the positioning image comprises a positioning object;
executing a field positioning module through the processor to analyze positioning coordinate information and the reference depth information of the positioning object in the positioning image through the field positioning module, so as to match a camera coordinate system of the depth camera with a robotic arm coordinate system of the surgical robotic arm.

13. The surgical robotic arm control method according to claim 12, wherein the surgical robotic arm control system is disposed around an operating table, and there is a fixed position relationship between the surgical robotic arm, the first image capturing unit, and the operating table, wherein matching the camera coordinate system of the depth camera with the robotic arm coordinate system of the surgical robotic arm comprises:
matching the camera coordinate system of the depth camera with the robotic arm coordinate system of the surgical robotic arm through the processor according to the fixed position relationship, the positioning coordinate information, and the reference depth information.

14. The surgical robotic arm control method according to claim 12, further comprising:
executing an object detection and recognition module through the processor to analyze the first target image and corresponding target depth information in the field image through the object detection and recognition module to obtain coordinate information of the target object.

15. The surgical robotic arm control method according to claim 14, wherein obtaining the robotic arm movement information comprises:
executing a space recognition module through the processor to analyze the first target image, the target depth information, at least one obstacle image, and at least one piece of obstacle depth information in the field image through the space recognition module to obtain effective spatial feature weight information; and
generating the robotic arm movement information through the processor according to the coordinate information and the effective spatial feature weight information.

16. The surgical robotic arm control method according to claim 14, wherein obtaining the robotic arm rotation information comprises:
executing an object angle recognition module through the processor to analyze the second target image through the object angle recognition module to obtain angle information of the target object; and
generating the robotic arm rotation information through the processor according to the angle information.

17. The surgical robotic arm control method according to claim 16, wherein the target object is a hand object, and the hand object comprises a feature block, wherein obtaining the angle information of the target object comprises:
analyzing a feature block image in the second target image through the object angle recognition module to obtain the angle information of the target object.

18. The surgical robotic arm control method according to claim 16, wherein the target object is an instrument object, and the instrument object comprises a groove section, wherein obtaining the angle information of the target object comprises:
analyzing a groove section image in the second target image through the object angle recognition module to obtain the angle information of the target object.

19. The surgical robotic arm control method according to claim 16, further comprising:
outputting a plurality of first feature weights through the object detection and recognition module according to the field image;
outputting a plurality of second feature weights through the object angle recognition module according to the second target image; and
comparing the first feature weights and the second feature weights through the processor to determine standard recognition information corresponding to the target object.

20. The surgical robotic arm control method according to claim 11, further comprising:
providing a selection signal through an input unit; and
selecting an image range of the first target image corresponding to the target object from the field image through the processor according to the selection signal.

* * * * *